US00PP27893P2

(12) United States Plant Patent
Kordes

(10) Patent No.: US PP27,893 P2
(45) Date of Patent: Apr. 18, 2017

(54) CLIMBING ROSE PLANT NAMED 'KORPUCOBLU'

(50) Latin Name: *Rosa hybrida*
Varietal Denomination: KORpucoblu

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 14/757,184

(22) Filed: Dec. 1, 2015

(51) Int. Cl.
*A01H 5/02* (2006.01)

(52) U.S. Cl.
USPC ..... Plt./109

(58) Field of Classification Search
USPC ..... Plt./109
CPC ..... A01H 5/0222
See application file for complete search history.

*Primary Examiner* — Kent L Bell

(57) ABSTRACT

'KORpucoblu' is a new and distinct variety of *Rosa hybrida* which is characterized by the combination of a climbing growth habit, vigorous growth, an abundance of large and very-double flowers, lavender flower color, and excellent disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORpucoblu'.

BACKGROUND OF THE INVENTION

The present invention relates to a new and distinct *Rosa hybrida*, climbing rose cultivar, which has been given the variety denomination of 'KORpucoblu'.

Parentage: The *Rosa hybrida* variety 'KORpucoblu' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, continuous flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORpucoblu' from all other varieties known to the inventor.

'KORpucoblu' is a seedling selection which resulted from the controlled pollination of two unnamed breeding lines, both developed and owned by the same inventor, during the summer of 2004. As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2005 from the seedling beds due to its superior characteristics and asexually propagated for further evaluation. This new and distinctive rose variety was given the name 'KORpucoblu'.

Asexual Reproduction: The first asexual propagation of 'KORpucoblu' was performed in July of 2005 at the inventor's nursery in Offenseth-Sparrieshoop, Germany. Subsequently, 'KORpucoblu' has been successfully propagated by stem cuttings and grafting in Jackson County, Oreg. These initial and other subsequent propagations conducted in controlled environments demonstrate that 'KORpucoblu' reproduces true to type in successive generations of asexual reproduction.

SUMMARY OF THE INVENTION

The following characteristics have been repeatedly observed and represent the distinguishing characteristics of the new *Rosa hybrida* cultivar 'KORpucoblu'. These traits, in combination, distinguish 'KORpucoblu' as a new and distinct cultivar.

1. *Rosa hybrida* 'KORpucoblu' exhibits a climbing growth habit; and
2. *Rosa hybrida* 'KORpucoblu' exhibits vigorous growth; and
3. *Rosa hybrida* 'KORpucoblu' exhibits excellent disease resistance; and
2. *Rosa hybrida* 'KORpucoblu' exhibits an abundance of flowers; and
3. *Rosa hybrida* 'KORpucoblu' exhibits a very-double petal count; and
4. *Rosa hybrida* 'KORpucoblu' exhibits a large flower size; and 5. *Rosa hybrida* 'KORpucoblu' exhibits a lavender flower color, at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpucoblu', taken from two year old plants.

DETAILED BOTANICAL DESCRIPTION

The following is a detailed botanical description of a new and distinct variety of *Rosa hybrida* known as 'KORpucoblu', based upon field observations made in October of 2015, from two year old plants, grown in-ground, at a nursery in Jackson County, Oreg.

Those skilled in the art will appreciate that certain characteristics will vary with older or, conversely, with younger plants. 'KORpucoblu' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORpucoblu' and comparisons with other varieties of *Rosa hybrida* are provided below.

General plant description:

*Growth rate*.—Vigorous.

*Growth habit*.—Climbing.

*Mature dimensions*.—Approximately 220 cm tall and 100 cm wide.

*Cold hardiness*.—Grown successfully in USDA Hardiness Zone 6.

*Propagation*.—Grafting and stem cuttings.

*Disease resistance*.—Excellent resistance to powdery mildew (*Sphaerotheca pannosa*), blackspot (*Diplocarpon rosae*) and rust (*Phragmidium* sp.) diseases under normal growing conditions in Jackson County, Oreg.

Root system: Fibrous.

Stems:

*Stem color*.—Immature stems are Yellow-Green Group 146C; mature stems are Yellow-Green Group 146B.

*Anthocyanin intonations*.—Greyed-Purple Group 183B present on new growth.

*Stem surface texture*.—Both immature and mature stems exhibit a smooth texture.

*Stem dimensions*.—Typical mature stems are approximately 200 cm long and 30 mm in diameter near the base.

*Prickles*.—Incidence — Present; 9 prickles per 10 cm of stem, on average. Size — Average length is 6 mm. Immature prickle color — Greyed-Orange Group 172B. Mature prickle color — Greyed-Orange Group N170B, senescing to Greyed-Orange Group 165C. Anthocyanin intonations — Greyed-Red Group 180A present on mature prickle margins. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—180 mm long and 140 mm wide, on average.

*Abundance*.—A range of 80 to 120 leaves.

*Stipules*.—Size — 15 mm long and 5 mm wide. Stipule color — Yellow-Green Group 146D. Anthocyanin intonations — None. Stipitate glands — Limited; few glands present at margins. Margins — Glandular toothed. Texture, adaxial and abaxial surfaces — Glabrous. Apex — Apiculate. Base — Fused to the petiole.

*Petiole*.—Length — Average 7 mm. Diameter — Average 3 mm. Petiole color, adaxial and abaxial surfaces — Yellow-Green Group 146D. Margins — A few stipitate glands present. Anthocyanin intonations — None. Prickles — A single small prickle. Stipitate glands — Limited number present on margins. Texture — Rugose. Strength — Strong.

*Rachis*.—Length — Average 30 mm. Diameter — Average 2 mm. Color — Yellow-Green Group 146C. Anthocyanin intonations — None. Margins — Limited stipitate glands. Prickles — A few small prickles underneath. Stipitate glands — Present on margins and, occasionally, on abaxial surface.

*Leaflets*.—Quantity — Normally 7 leaflets on normal leaves in middle of the stem. Dimensions — Average size of the terminal leaflet is 60 mm long and 50 mm wide. Shape — Broadly ovate. Apex — Cuspidate. Base — Obtuse. Margins — Finely serrated; slightly undulating. Texture, adaxial surface — Semi-glossy and smooth; glabrous. Texture, abaxial surface — Matte and leathery; glabrous. Juvenile foliage color, adaxial surface — Yellow-Green Group 146C. Juvenile foliage color, abaxial surface — Yellow-Green Group 146C. Mature foliage color, adaxial surface — Yellow-Green Group 147A. Mature foliage color, abaxial surface — Yellow-Green Group 147B. Anthocyanin intonations — Greyed-Purple Group 185A. Present on both adaxial and abaxial surfaces of new, juvenile leaflets. Venation — Reticulate. Petiolule — Dimensions — 2 mm long. Petiolule color, adaxial and abaxial surfaces — Yellow-Green Group 146B. Prickles — None present. Texture, adaxial and abaxial surfaces — Leathery.

Inflorescence:

*Inflorescence type*.—Slightly pendulous to upright panicles.

*Blooming habit*.—Continuous; floriferous.

*Quantity of flowers*.—Generally 4 flowers on panicles.

*Size*.—Panicles are 160 mm tall and 100 mm wide, on average.

*Peduncle*.—Length — 40 to 50 mm average length. Diameter — 4 to 5 mm average diameter. Color — Yellow-Green Group 146C. Anthocyanin intonations — Greyed-Purple Group 184C. Strength — Strong. Texture — Rugose.

Flowering laterals: Present below the initiation of inflorescence. Generally 1 to 2 flowering laterals are present, with 1 to 2 flowers per flowering shoot.

Bud:

*Bud form*.—Short; pointed ovoid.

*Size*.—Upon opening, 20 mm in length from base of receptacle to distal end of bud and 15 mm diameter at its widest point.

*Texture*.—Smooth.

*Color, as sepals first unfold*.—Red Group 60B, with basal portion of outer petals colored Yellow-Green Group 147D.

*Color when one-quarter open, inner side*.—Violet Group 85A.

*Color when one-quarter open, outer side*.—Purple Group 78D.

Flower:

*Pedicel*.—Surface — Fine hairs and stipitate glands are present. Length — 30 to 40 mm, on average. Diameter — 3 to 4 mm, on average. Color — Yellow-Green Group 146D. Anthocyanin intonations — Greyed-Purple Group 146B to 146C. Strength — Somewhat strong. Texture — Rugose.

*Calyx*.—General — Comprised of five polysepalous sepals, with weak foliaceous appendages present on three of the five sepals. Diameter of calyx — 10 mm, at anthesis. Sepals — Color, adaxial and abaxial surfaces — Yellow-Green Group 146B. Anthocyanin intonations — Greyed-Purple 187C to 187D, present on the abaxial surface. Size — 15 to 18 mm long and 8 to 10 mm wide, on average. Apex — Apiculate. Base — Flat at union with receptacle. Quantity — Five. Texture, adaxial surface — Pubescent. Texture, abaxial surface — With stipitate glands. Margins — Pubescent with stipitate glands. Stipitate glands — Limited.

*Corolla*.—General shape of corolla — Rosette. Shape of corolla when viewed from the side — Upon opening, upper portion — Flattened convex. Upon opening, lower portion — Flattened convex. Open flower, upper portion — Flattened convex. Open flower, lower portion — Flattened convex. Dimensions — Large for a climbing rose. When open, the average flower diameter is 80 mm and the average flower height is 40 mm. Fragrance — Light. Duration — On the plant 5 to 8 days. Senesced petals drop away cleanly. Petals — Petal count — Exhibits very-double flowers with approximately 50 petals under normal conditions. Petal reflex — Somewhat reflexed. Timing of petal reflex — Simultaneously. Petal margin — Entire. Petal shape — Obtuse. Apex — Obtuse. Base — Obtuse. Dimensions — 40 mm long and 30 mm wide. Texture, inner surface — Smooth. Texture, outer surface — Smooth. Petal color, upon opening — Outermost petals, outer surface — Purple-Violet Group N81C. Outermost petals, inner surface — Purple-Violet Group N81C. Innermost petals, outer surface — Marginal zone — Red-Purple Group 72B. Middle zone — Red-Purple Group 72B. Basal zone — Purple Group 77C. Innermost petals, inner surface — Marginal zone — Red-Purple Group 72A. Middle zone — Red-Purple Group 72A. Basal zone — Purple Group 77B. Basal petal spots, upon opening — Basal petal spot, outermost petals — None observed. Basal petal spot, innermost petals — Dimensions — 4 mm high and 3 mm wide; occasionally extending up to middle zone along the midrib. Outer surface — White Group 155C. Inner surface — White Group 155A. Petal color, after opening — Outermost petals, outer surface — Purple-Violet Group N78D. Outermost petals, inner surface — Purple-Violet Group N81D. Innermost petals, outer and inner surfaces — Marginal zone — Purple Group N78B. Middle zone — Purple-Violet Group N81D. Basal zone — Purple-Violet Group N81D. Basal petal spots, after opening — Basal petal spot, outermost petals — Dimensions — 5 mm high and 5 mm wide. Color, outer surface — White Group N155A. Color, inner surface — White Group 155A. Basal petal spot, innermost petals — Dimensions — 5 mm high and 3 mm wide. Outer surface — White Group 155A. Inner surface — White Group 155A. General Tonality — Purple Group 77C, at anthesis, and fading to Violet Group 84B after 5 days. Petaloids — Quantity — 10 petaloids per flower, on average. Dimensions — Highly variable; approximately 10 to 20 mm long and 4 to 10 mm wide. Color, outer surfaces — Marginal zone — Purple Group N79C, with center margin White Group N155B. Middle zone — Purple-Violet Group N81D. Basal zone — Purple-Violet Group N81D. Color, inner surfaces — Purple Group N79C. Margins — Entire. Shape — Obovate to Spatulate; highly irregular. Apex — Obtuse. Base — Attenuate. Texture, inner and outer surfaces — Smooth.

Reproductive Organs:

*Stamens*.—Quantity — Approximately 100, on average, and regularly arranged around the styles. Anthers — Shape — Reniform. Dimensions — 2 mm long and 1 mm wide, on average. Color — Greyed-Yellow Group 162D. Pollen — Scarce. Pollen Color — Greyed-Yellow Group 162A. Filaments — Color — Greyed-Yellow Group 162B at the base, and Green-Yellow Group 1B. Length — 4 mm.

*Pistils*.—Quantity — Approximately 40. Stigmas — Dimensions — 1 mm long and 1 mm wide. Location — Slightly inferior to anthers. Color — Greyed-Yellow Group 160A. Styles — Length — Approximately 4 mm long. Color — Red Group 53A.

*Ovary*.—Dimensions — 8 mm long and 5 mm in diameter. Color — White Group 155B.

*Receptacle*.—Shape — Funnel-shaped. Dimensions — Approximately 12 mm high and 8 mm wide. Surface — Pubescent with stipitate glands. Color — Yellow-Green Group 146B with intonations of Greyed-Purple Group 183A to 183B. Texture — Glabrous.

Hips and seed formation:

*Size*.—25 mm.

*Color*.—Yellow-Green Group 146D.

*Texture*.—Smooth.

Comparisons with the Parents

The new rose plant may be distinguished from its seed parent, an unnamed breeding line, by the following combination of characteristics:

1. 'KORpucoblu' exhibits a large flower size for a climbing rose, whereas the seed parent exhibits a medium flower size.
2. 'KORpucoblu' exhibits a very double petal count, whereas the seed parent exhibits a semi-double petal count.

3. 'KORpucoblu' exhibits vigorous plant growth, whereas the seed parent exhibits moderate plant vigor.

The new rose plant may be distinguished from its pollen parent, an unnamed breeding line, by the following combination of characteristics:

1. 'KORpucoblu' exhibits a lavender flower color, whereas the pollen parent exhibits a violet flower color.
2. 'KORpucoblu' exhibits light fragrance, whereas the pollen parent exhibits intense fragrance.
3. 'KORpucoblu' exhibits excellent disease resistance, whereas the pollen parent exhibits average disease resistance.

Comparisons with Similar *Rosa hybrida* Cultivars Known to the Inventor

For a comparison, several physical characteristics of the rose variety 'KORfriedhar', a rose variety from the same inventor described and illustrated in U.S. Plant Pat. No. 23,555 are compared to 'KORpucoblu' in Chart 1.

CHART 1

| Characteristic | 'KORpucoblu' | 'KORfriedhar' |
|---|---|---|
| Growth Habit. | Climbing | Upright to bushy. |
| General tonality of flower, at anthesis. | Purple Group 77C. | Violet Group 85A to 85B. |
| Incidence of prickles. | 9 per 10 cm of stem. | 5 per 10 cm of stem. |

That which is claimed:

1. A new and distinct variety of rose plant named 'KORpucoblu', as described and illustrated herein.

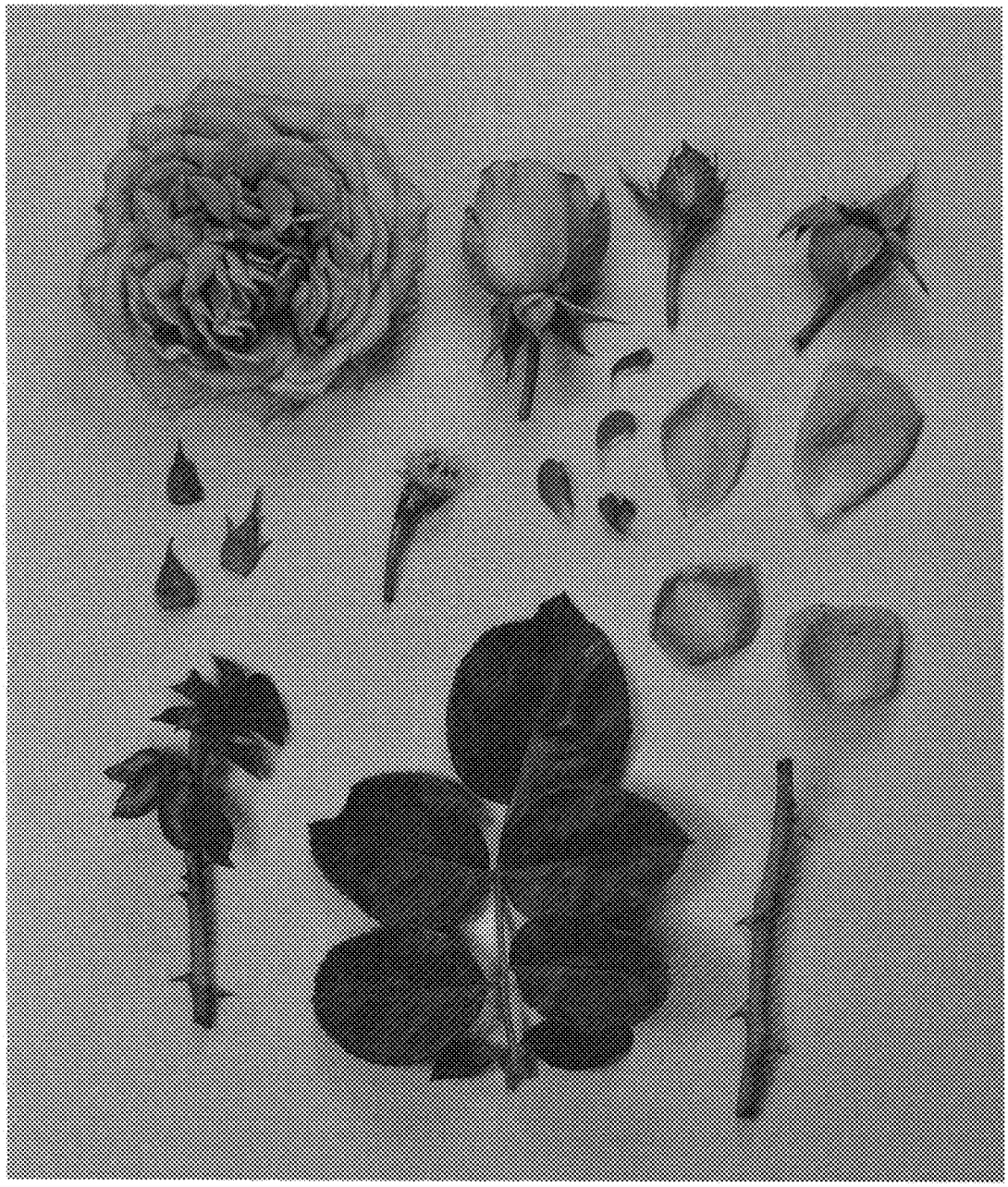

* * * * *